US011857383B2

(12) United States Patent
Johnson et al.

(10) Patent No.: US 11,857,383 B2
(45) Date of Patent: Jan. 2, 2024

(54) WASHING APPLIANCE AND METHODS OF USING

(71) Applicant: INNOVATIVE HEALTH, Scottsdale, AZ (US)

(72) Inventors: Kevin Johnson, Peoria, AZ (US); Alex Carson, Scottsdale, AZ (US); Chris Wolfbrandt, Phoenix, AZ (US); Blessan Joseph, Chandler, AZ (US); Rafal Chudzik, Peoria, AZ (US)

(73) Assignee: INNOVATIVE HEALTH, Scottsdale, AZ (US)

(*) Notice: Subject to any disclaimer, the term of this patent is extended or adjusted under 35 U.S.C. 154(b) by 0 days.

(21) Appl. No.: 18/163,226

(22) Filed: Feb. 1, 2023

(65) Prior Publication Data
US 2023/0240794 A1 Aug. 3, 2023

Related U.S. Application Data

(60) Provisional application No. 63/305,430, filed on Feb. 1, 2022.

(51) Int. Cl.
*A61B 90/70* (2016.01)

(52) U.S. Cl.
CPC ........ *A61B 90/70* (2016.02); *A61B 2090/701* (2016.02)

(58) Field of Classification Search
None
See application file for complete search history.

(56) References Cited

U.S. PATENT DOCUMENTS

| 5,425,815 | A | 6/1995 | Park et al. |
| 6,447,446 | B1* | 9/2002 | Smith ................ A61B 1/00135 600/118 |
| 10,772,491 | B2* | 9/2020 | Chouinard ............. A61B 1/123 |
| 2004/0091389 | A1 | 5/2004 | Malkin et al. |
| 2012/0048883 | A1 | 3/2012 | Heckenberger et al. |
| 2015/0118107 | A1 | 4/2015 | Sunkara et al. |

FOREIGN PATENT DOCUMENTS

| CN | 112057655 A | 12/2020 |
| JP | 2004215930 A | 8/2004 |
| KR | 101907353 B1 | 12/2018 |

OTHER PUBLICATIONS

International Search Report International Application No. PCT/US23/61795 dated May 2, 2023.

* cited by examiner

*Primary Examiner* — Rita P Adhlakha
(74) *Attorney, Agent, or Firm* — POLSINELLI PC

(57) ABSTRACT

A washing appliance for efficient and through cleaning of medical devices and methods of using the appliance are disclosed. The appliance can clean exteriors of medical devices, and lumens of devices comprising a lumen such as cathlab devices.

18 Claims, 13 Drawing Sheets

WASHING APPLIANCE AND METHODS OF USING

CROSS-REFERENCE TO RELATED APPLICATIONS

This application claims priority from Provisional Application No. 63/305,430, filed Feb. 1, 2022, the entire contents of which are hereby incorporated by reference.

FIELD OF THE INVENTION

The present disclosure provides a washing appliance for washing a device and methods of using the appliance.

BACKGROUND OF THE INVENTION

The estimated annual cost of waste in the US health care system ranges from $760 billion to $935 billion, accounting for approximately 25% of total health care spending, and the projected potential savings from interventions that reduce waste, excluding savings from administrative complexity, ranges from $191 billion to $286 billion, representing a potential 25% reduction in the total cost of waste. Further, medical waste constitutes a special class of hazardous pollutants causing serious environmental impact. The disposal of untreated health care wastes in landfills can lead to the contamination of drinking, surface, and ground waters if those landfills are not properly constructed.

Single-use medical device reprocessing is effective in reducing the volume of waste produced and reducing costs to hospitals and reduce the environmental impact of medical waste. On average, reprocessed single-use medical devices can offer 50% cost savings. There will continue to be a need for reprocessed single-use medical devices as the commercial reprocessing industry expands. A variety of devices for disinfection of surgical instruments, forceps, endoscopes, and other medical devices exist, all of which are used on devices that are not labeled single-use. The devices include autoclaves and endoscope reprocessing machines. However, there are currently no machines on the market that effectively disinfect single-use medical devices such as medical device used during cardiovascular procedures (cath lab) and accessory devices.

Therefore, there is a need for devices, machines, and methods capable of efficiently and effectively reprocessing single-use medical devices and accessory devices such as those used during cardiovascular procedures.

SUMMARY OF THE INVENTION

One aspect of the instant disclosure encompasses a washing appliance for washing a medical device. The washing appliance comprises a rinse tank, one or more spray assemblies, and one or more manifolds. In some aspects, the washing appliance further comprises a pressure pump or compressor disposed between the spray assemblies and a spray fluid source, wherein the pressure pump or compressor causes the spray fluid to spray from the one or more nozzles at a predetermined pressure or flow rate.

In some aspects, the medical device is a medical device used during a cardiovascular procedure (cath lab) and accessory devices. For instance, the medical device can be a catheter, an endoscope, a closure device, an accessory device to a catheter or endoscope, or any combination thereof. In some aspects, the medical device is a catheter, an endoscope, a dilator, an introducer, medical tubing, racetrack tubing, a guide wire, a cable, or any combination thereof. The medical device can be an unused originally manufactured device (OM), a used OM device, an unused reprocessed device, or a used reprocessed device.

The rinse tank comprises a rinse tank interior space defined by a rinse tank top, a rinse tank bottom, and rinse tank walls; an access door for reversibly sealing a rinse tank opening in the walls; and a drain in the rinse tank bottom;

A spray assembly comprises a spray tube extending through a spray tube opening in the rinse tank top into the rinse tank interior space along a vertical longitudinal axis extending from the rinse tank top to the rinse tank bottom. The spray tube comprises a spray fluid opening at a spray tube proximal end external to the rinse tank, a spray tube distal end in the rinse tank interior space, wherein the spray fluid opening is in fluid communication with a source of spray fluid. The spray tube also comprises one or more nozzles attached to the spray tube.

The spray assembly can comprise seven pairs of nozzles, wherein a first nozzle in a pair of nozzles is positioned opposite a second nozzle in the pair of nozzles. In some aspects, the washing appliance comprises three or more pairs of spray assemblies and two or more manifolds disposed alternatively between the pairs of spray assemblies. In other aspects, the washing appliance comprises three pairs of spray assemblies and two manifolds disposed alternatively between the pairs of spray assemblies. In some aspects, the washing appliance comprises five pairs of spray assemblies and four manifolds disposed alternatively between the pairs of spray assemblies.

The manifold is attached in the interior space of the rinse tank 10 at a first surface of the manifold to a manifold support structure at the rinse tank top, wherein the manifold comprises device attachment points at a second surface of the manifold opposite the first surface, wherein the attachment points are operable to removably accept a device attachment accessory. In some aspects, the manifold comprises forty-eight device attachment points. The device attachment accessory is operable to hang a device in a volume of space extending along the longitudinal axis below the manifold in the rinse tank interior space. The one or more nozzles 400 are operable to spray the spray fluid into the volume of space.

In some aspects, the manifold 500 comprises protruding edges 550 and the manifold support structure 520 comprises channels 560 operable to engage the protruding edges 550 of the manifold 500. In some aspects, the manifold support structure 520 further comprises a locking mechanism 570 operable to secure the manifold 500 to the manifold support structure 520.

In some aspects, the device is a lumen device comprising a Luer connector 640 in fluid communication with the lumen of the device. When the device is a lumen device, the washing appliance can further comprise one or more lumen devices 600 comprising a Luer connector 640 attached to the Luer connector attachment accessory 535. When the device is a lumen device, the washing appliance can also further comprises a pressure pump or compressor disposed between the wash fluid opening and the wash fluid source, wherein the pressure pump or compressor causes the wash fluid to flow through the lumen of the device at a predetermined flow rate.

The manifold 500 can further comprise a wash fluid adapter 590 connected to a wash fluid opening 580 in the manifold 500 and extending through a wash fluid adapter opening 595 in the rinse tank walls 150. One or more of the attachment points 530 can comprise a wash fluid delivery opening 596 in fluid communication with a source of wash fluid through a wash fluid flow path extending from the wash fluid delivery opening 595 to the source of wash fluid through a manifold channel in the manifold 500 extending between the wash fluid delivery opening 596 and the wash fluid opening 580 or the wash fluid adapter opening 595. In some aspects, the device attachment accessory 535 is a Luer connector attachment accessory connected to the attachment point 530.

The wash or spray fluid can comprise a cleaning and/or drying agent. Further, the wash or spray fluid can be liquid or air. In some aspects, the washing appliance further comprises connectors, valves, sensors such as pressure sensors and flow meters, seals, gaskets, and other fluid containment and control elements to direct the spray fluid and wash fluid during operation of the washing appliance.

Another aspect of the instant disclosure encompasses a method of cleaning the exterior of a device comprising a lumen using a washing appliance. The washing appliance can be as described herein above. The method comprises the steps of (a) attaching one or more devices to be washed to device attachment accessories of a manifold; (b) attaching and securing the manifold to the manifold support structure in the interior space of the rinse tank; (c) attaching the spray fluid opening of the spray assembly to a source of cleaning fluid by attaching piping extending from the spray fluid opening to the source of cleaning fluid and spraying the exterior surfaces of the device with cleaning fluid to thereby washing the exterior surfaces of the device; and (d) optionally drying the device by spraying the device with drying fluid.

In some aspects, the device is a lumen device. When the device is a lumen device, the method can further comprise cleaning the lumen of the device concurrently or sequentially with cleaning the exterior of the device. Cleaning the lumen of the device can comprise the steps of: (a) attaching the wash fluid opening of the manifold to a source of cleaning fluid by attaching piping extending from the wash fluid opening of the manifold to the source of cleaning fluid; (b) flushing the lumen of the device with the cleaning fluid at a predetermined flow rate or pressure; and (c) optionally drying the lumen of the device by flushing the lumen of the device with drying fluid.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
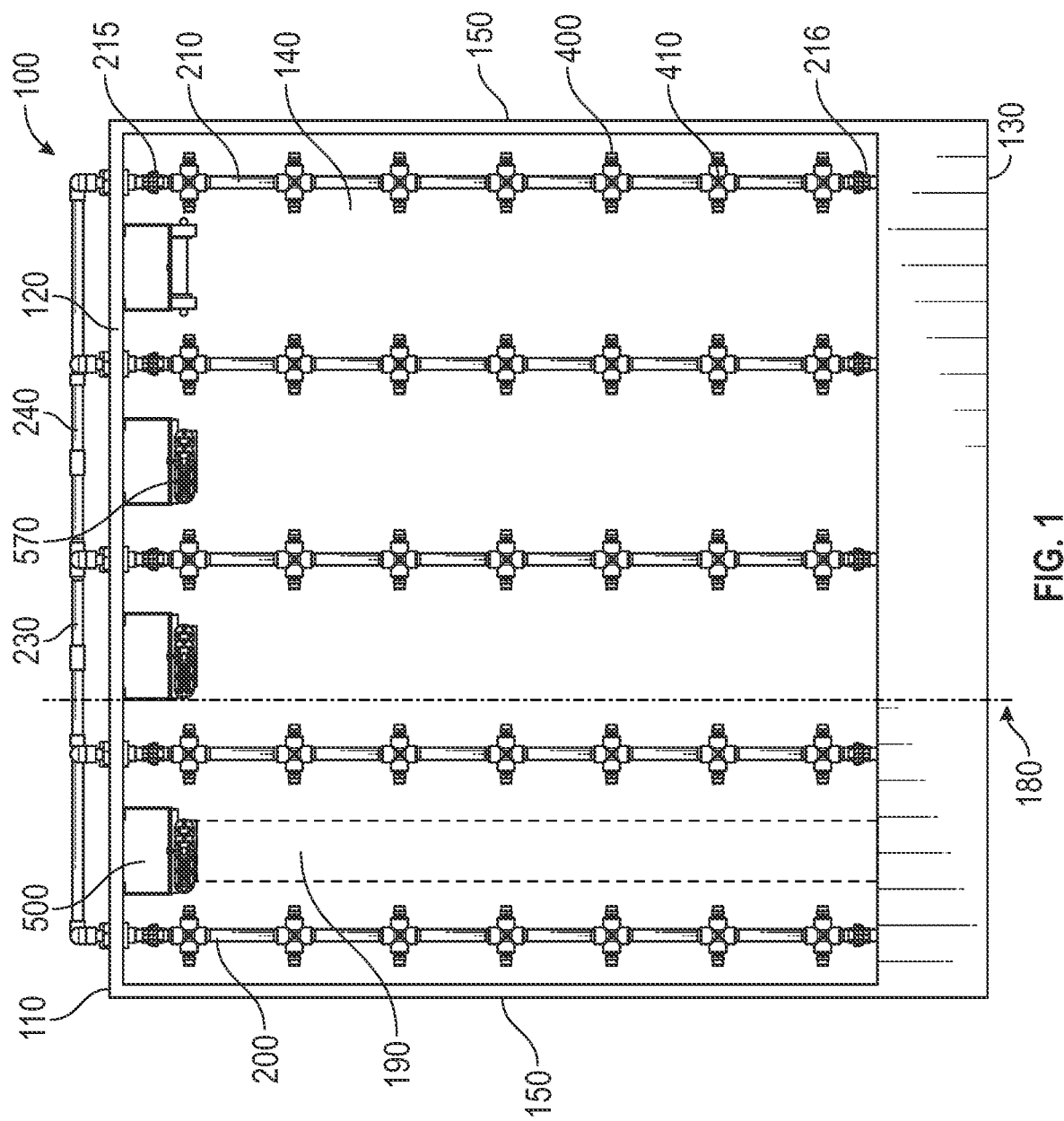
FIG. 1 is a front view of a washing appliance of the instant disclosure comprising four manifolds. The access door is not shown.

The present disclosure encompasses washing appliances, washing systems, washing controllers, and methods of using thereof designed, developed, and built by the inventors. The appliances, systems, and controllers are capable of high throughput cleaning of medical devices and accessory devices normally relegated to waste such as those used during cardiovascular procedures. The ability to clean medical devices and accessories can be used during reprocessing of single-use devices in conjunction with other reprocessing methods such as those used for inspection of lumen devices for occlusions in the lumen.

The washing appliances, washing systems, washing controllers, and methods of using thereof will be understood from the accompanying drawings, taken in conjunction with the accompanying description. It is noted that, for purposes of illustrative clarity, certain elements in various drawings may not be drawn to scale. Several variations of the system are presented herein. It should be understood by those of skill in the art, that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this invention that the features, elements, and/or functions of one variation may be incorporated into another variation as appropriate, unless described otherwise.

I. Washing Appliance

One aspect of the present disclosure encompasses a washing appliance for washing devices. The washing appliance comprises a rinse tank, manifolds for suspending devices to be washed in the washing appliance, and spray assemblies for spraying devices suspended in the rinse tank.

(a) Devices

The washing appliance of the instant disclosure can be used to wash any device, including single-use medical devices used during cardiovascular procedures (cath lab) and accessory devices. Accordingly, as used herein, the term "medical device" comprises a medical device used during a medical procedure and any other accessory that may be used during the procedure. In some aspects, the washing appliance is used to wash a medical device used during cardiovascular procedures (cath lab) and accessory devices. Non-limiting examples of medical devices and accessories include medical devices comprising lumens, catheters, endoscopes, dilators, dilator accessories, introducer sheaths, guidewires, balloons, vascular closure devices, atherectomy devices, fractional flow reserve (FFR) wires, racetrack tubing, cables and wiring, medical tubing, and hypodermic, transseptal, and other needles.

In some aspects, the medical device comprises one or more lumen such as catheters and endoscopes. Catheters and endoscopes are extensively used to perform an array of minimally invasive procedures. An endoscope is an illuminated optical, typically slender, and tubular instrument (a type of borescope) used to look deep into the body by way of openings such as the mouth or anus. Endoscopes use tubes which are only a few millimeters thick to transfer illumination in one direction and high-resolution images in real time in the other direction, resulting in minimally invasive surgeries. Endoscopes are used to examine the internal organs like the throat or esophagus. Specialized endoscopes are named after their target organ. Examples include the cystoscope (bladder), nephroscope (kidney), bronchoscope (bronchus), arthroscope (joints) and colonoscope (colon), and laparoscope (abdomen or pelvis). Endoscopes can be used to visually examine and diagnose or assist in surgery such as an arthroscopy. For non-medical uses, similar instruments are called borescopes. Some endoscopes comprise working channels comprising a lumen to allow entry of medical instruments or manipulators. As used herein, the term "lumen device" is used to refer to a medical device comprising a lumen and accessories used during procedures employing the lumen device.

A catheter is a thin tube made from medical grade materials serving a broad range of functions in medicine. Catheters can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications. In most uses, a catheter is a thin, flexible tube ("soft" catheter) though catheters are available in varying levels of stiffness depending on the application. A catheter left inside the body, either temporarily or permanently, may be referred to as an "indwelling catheter" (for example, a peripherally inserted central catheter). A permanently inserted catheter may be referred to as a "permcath." Catheters can be inserted into a body cavity, duct, vessel, brain, skin, or adipose tissue. Functionally, catheters allow drainage and administration of fluids or gases, access by surgical instruments, and can also perform a wide variety of other tasks depending on the type of catheter.

Placement of a catheter into a particular part of the body may allow:
  Administration of fluids (i.e., heparinized saline, contrast dyes) during an electrophysiology, or related, study;
  Fluid sampling during an electrophysiology, or related, study;
  Direct blood pressure measurement during an electrophysiology, or related, study;
  Angioplasty, angiography, balloon septostomy, balloon sinuplasty, cardiac, catheter ablation;
  Draining urine from the urinary bladder as in urinary catheterization, e.g., the intermittent catheters or Foley catheter or even when the urethra is damaged as in suprapubic catheterization;
  Drainage of urine from the kidney by percutaneous (through the skin) nephrostomy;
  Drainage of fluid collections, e.g. an abdominal abscess;
  Drainage of air from around the lung (pigtail catheter);
  Administration of intravenous fluids, medication or parenteral nutrition with a peripheral venous catheter;
  Direct measurement of blood pressure in an artery or vein;
  Direct measurement of intracranial pressure;
  Direct measurement of blood flow;
  Intravascular ultrasound;
  Optical coherence tomography (OCT) imaging;
  Near-infrared spectoscopy (NIRS);
  Administration of anesthetic medication into the epidural space, the subarachnoid space, or around a major nerve bundle such as the brachial plexus;
  Administration of oxygen, volatile anesthetic agents, and other breathing gases into the lungs using a tracheal tube;
  Subcutaneous administration of insulin or other medications, with the use of an infusion set and insulin pump;
  Administering drugs or fluids into a large-bore catheter positioned either in a vein near the heart or just inside the atrium;
  Measuring pressures in the heart;
  Inserting fertilized embryos from in vitro fertilization into the uterus;
  Providing quick access to the central circulation of premature infants using an umbilical line;
  Attaching catheters to various other devices;
  Hemodialysis using a double or triple lumen, external catheter; and
  Artificial insemination.

Non-limiting examples of needles used in the medical field include:
  Abrams' needle: A biopsy needle designed to reduce the danger of introducing air into tissues; used in pleural biopsy.
  Agar cutting needle: A needle with a sharpened punch end and an obturator to pick up and transfer a sample of agar media.
  Aneurysm needle: A needle with a handle, used in ligating blood vessels.
  Aspirating needle: A long, hollow needle for removing fluid from a cavity.
  Brockenbrough needle: A curved steel transseptal needle within a Brockenbrough transseptal catheter; used to puncture the interatrial septum.
  Cataract needle: A needle used in removing a cataract.
  Chiba needle: A common type of thin, flexible biopsy needle with a small-diameter needle and a stylet in the needle lumen.
  Cope's needle: A blunt-ended hook-like needle with a concealed cutting edge and snare, used in biopsy of the pleura, pericardium, peritoneum, and synovium.
  Deschamps' needle: A needle with the eye near the point, and a long handle attached; used in ligating deep-seated arteries.
  Discission needle: A special form of cataract needle.
  Emulsifying needle: A small tube with luer fittings at each end for mixing a liquid and an emulsifying agent by pushing the liquids through the tubing into opposing syringes. A simple type of static mixer.
  Hagedorn's needles: Surgical needles that are flat from side to side and have a straight cutting edge near the point and a large eye.
  Hasson trocar: A blunt trocar inserted into the peritoneal cavity after a celiotomy. Used for insufflation and introduction of a laparoscope.
  Knife needle: A slender knife with a needle like point, used in discission of a cataract and other ophthalmic operations, as in goniotomy and goniopuncture.
  Ligature needle: A slender steel needle with a long handle and an eye in its curved end, used for passing a ligature underneath an artery.

Menghini needle: A needle that does not require rotation to cut loose the tissue specimen in a biopsy of the liver. This represented a significant advance in the previously slow and hazardous methods of liver biopsy.

Reverdin's needle: A surgical needle having an eye that can be opened and closed by means of a slide.

Seldinger needle: A needle with a blunt, tapered external cannula with a sharp obturator; used for the initial percutaneous insertion characteristic of the Seldinger technique for arterial or venous access.

Silverman needle: An instrument for taking tissue specimens, consisting of an outer cannula, an obturator, and an inner split needle with longitudinal grooves in which the tissue is retained when the needle and cannula are withdrawn.

Stop needle: A needle with a shoulder that prevents it from being inserted beyond a certain distance.

Transseptal needle: A needle used to puncture the interatrial septum in transseptal catheterization.

Tuohy needle: One in which the opening at the end is angled so that a catheter exits at an angle. The end of the Tuohy needle provides controlled penetration during the administering of spinal anesthesia and placement of an epidural spinal catheter.

Veress needle: Named for Janos Veress, a German doctor. A Veress needle is a spring-loaded needle originally used to drain ascites and evacuate fluid and air from the chest. Veress needles were later adapted to use in laparoscopy.

The diameter of a lumen in a medical device can range from about 0.1 to about 5 mm. For instance, the diameter of a lumen can range from about 0.001" to about 0.1", or from about 0.01" to about 0.05" internal diameter. The length of a lumen of a device can range from about 1 cm to a few meters. For instance, the length of a lumen can range from about 5 cm to about 5 meters, from about 20 cm to about 4 m, from about 50 cm to about 2 m. In some aspects, the length of a lumen can range from about 50 cm to about 150 cm. The gage of a needle can range from about 50 ga to about 5 ga, from about 40 ga to about 10 ga, or from about 30 ga to about 15 ga.

Some devices can comprise multiple lumens, each performing one or more functions. These lumens can serve as inflation ports, fluid-transfer channels, guidewire access points, or even steering lumens, among others. As such, devices can have one lumen, or can have multiple lumens. For instance, a device can have 1, 2, 3, 4, 5, 6, 7, 8, 9, or 10 or more lumens. The lumens can be a multi-lumen tube extruded or attached into a single tube or can be separately bundled inside a device.

(b) Rinse Tank

The washing appliance comprises a rinse tank. The rinse tank comprises an interior space defined by a top, a bottom, and walls. The rinse tank also comprises an opening in the walls, and an access door for reversibly sealing the opening. A drain in the bottom of the rinse tank is operable to drain wash and spray fluids from the washing appliance during operation. The rinse tank can be constructed from any appropriate material including chemically and biologically inert, easy to clean material. In some aspects, the rinse tank is partially of completely constructed of transparent material which can allow monitoring of the washing process during use.

Dimensions of the rinse tank can and will vary depending on the device to be washed and the number of devices to be washed in a single washing appliance among other variables. For instance, as the washing appliance is operable to suspend a device during washing, the rinse tank comprises a height capable of accommodating the full length of the device when suspended in the rinse tank. Additionally, the width and depth of the rinse tank will vary to accommodate the number of spray assemblies and manifolds that can accommodate the number of devices to be washed.

The opening of the rinse tank and the access door for reversibly sealing the opening is generally sufficiently wide to allow access to the internal components of the washing appliance, including the one or more spray assemblies and one or more manifolds. For instance, in one aspect of a method of using the washing appliance, a manifold can be removed from the rinse tank, loaded with devices to be washed, returned into and attached in the rinse tank, and removed again from the rinse tank to collect the washed device. Accordingly, an opening of the rinse tank is generally of a width and height that permits the loading and unloading of devices and accessories before and after washing such that the washed device can be collected without contaminating the washed device.

(c) Spray Assembly

The washing appliance of the instant disclosure comprises one or more spray assemblies disposed in the interior space of the rinse tank. A spray assembly comprises a spray tube disposed in the interior space of the rinse tank. The spray tube extends through a spray tube opening in the top of the rinse tank into the interior space of the rinse tank. The spray tube extends along a longitudinal axis extending from the top to the bottom of the rinse tank. The spray tube comprises a spray fluid opening at a spray tube proximal end external to the rinse tank and a spray tube distal end in the interior space of the rinse tank. The spray fluid opening is in fluid communication with a source of spray fluid. The spray assembly also comprises one or more spray nozzles attached to the spray tube. The one or more nozzles are in fluid communication with the source of wash fluid through the spray tube at the spray fluid opening.

As described in Section I(f) herein below, a washing appliance comprises at least one manifold defining a volume of space extending along the longitudinal axis below the manifold in the interior space of the rinse tank where the medical device or accessory to be washed hangs. Accordingly, the nozzles are generally operable to direct a spray stream towards the volume of space. Further, the length of the spray assembly, the number of spray assemblies, the number of spray nozzles, and the type of spray nozzle can and will vary depending on the height of the rinse tank, the length of the device to be washed, and the type of nozzle, among other variables, provided the combination of spray assembly length, the type of spray nozzle and the number of spray nozzles can provide a full coverage of the external surface of the device to be washed.

A washing appliance comprises any number of spray assemblies, provided the spray assemblies can provide a full coverage of the external surface of the device to be washed. A washing appliance can comprise 1, 2, 3, 4, 5, 6, 7, 8, 9, 10, or more spray assemblies directed to the volume of space below the manifold. In some aspects, the washing appliance comprises one spray assembly operable to direct the spray fluid into the volume of space below the manifold. In some aspects, the washing appliance comprises a pair of spray assemblies on either side of the manifold with the nozzles direct towards the volume of space where a device hangs. Such an arrangement allows for the one or more nozzles to be operable to spray the spray fluid from two directions into the volume of space to thereby provide complete coverage of the external surface of the device to be washed.

When the washing appliance comprises more than one manifold, the washing appliance can comprise one spray assembly disposed alternatively between the manifolds. For instance, when the washing appliance comprises more than one manifold, the washing appliance can comprise three or more pairs of spray assemblies and two or more manifolds disposed alternatively between the pairs of spray assemblies. In such an arrangement, each spray assembly disposed between a first and a second manifold can comprise a pair of spray nozzles wherein one spray nozzle is operable to spray the spray fluid to the volume of space below the first manifold and the other spray nozzle is directed to the volume of space below the second manifold.

In some aspects, the washing appliance comprises three or more spray assemblies and two or more manifolds disposed alternatively between the pairs of spray assemblies. In other aspects, the washing appliance comprises three spray assemblies and two manifolds disposed alternatively between the pairs of spray assemblies. In some aspects, the washing appliance comprises three spray assemblies and two manifolds disposed alternatively between the pairs of spray assemblies.

A spray assembly can comprise 1, 2, 3, 4, 5, 6, 7, 8, 9, 10, 11, 12, 13, 14, 15, 16, 17, 18, 19, 20 or more nozzles. In some aspects, the spray assembly comprises seven nozzles. In some aspects, the nozzles are arranged in pairs on the tube of the spray assembly, wherein one spray nozzle is operable to spray the spray fluid to the volume of space below the first manifold and the other spray nozzle is directed to the volume of space below the second manifold. A spray assembly can comprise 1, 2, 3, 4, 5, 6, 7, 8, 9, 10, 11, 12, 13, 14, 15, 16, 17, 18, 19, 20 or more pairs of nozzles. In some aspects, the spray assembly comprises seven pairs of nozzles.

Spray nozzles break the liquid into droplets, form the spray pattern, and propel the droplets in the proper direction. Nozzles can determine the amount of spray volume at a given operating pressure, travel speed, and spacing. The nozzle can be a factor in determining the amount of spray applied to an area, the uniformity of application, and the coverage obtained on the target surface among other variables. Selecting nozzles that produce the appropriate droplet size while providing adequate coverage at the intended application rate and pressure can be determined using methods known to individuals of skill in the art. Non-limiting examples of nozzle types include flat-fan nozzles, flood nozzles, rain drop nozzles, hollow core nozzles, full cone nozzles.

(d) Manifold

The washing appliance comprises one or more manifolds, wherein each manifold is operable to hang a device in a volume of space extending along the longitudinal axis below the manifold in the interior space of the rinse tank. The manifold is attached in the interior space of the rinse tank at a first manifold surface to a manifold support structure at the top of the rinse tank. The manifold can be attached to the top of the rinse vessel using any number of mechanical attachment methods. Non-limiting examples of mechanical attachment methods include glue, magnets, a notch, a groove, a hook and loop fastener, mated threads on the manifold and rinse vessel, nuts and bolts, clips, clamps such as band clamps, or any combination thereof.

Figure 12:
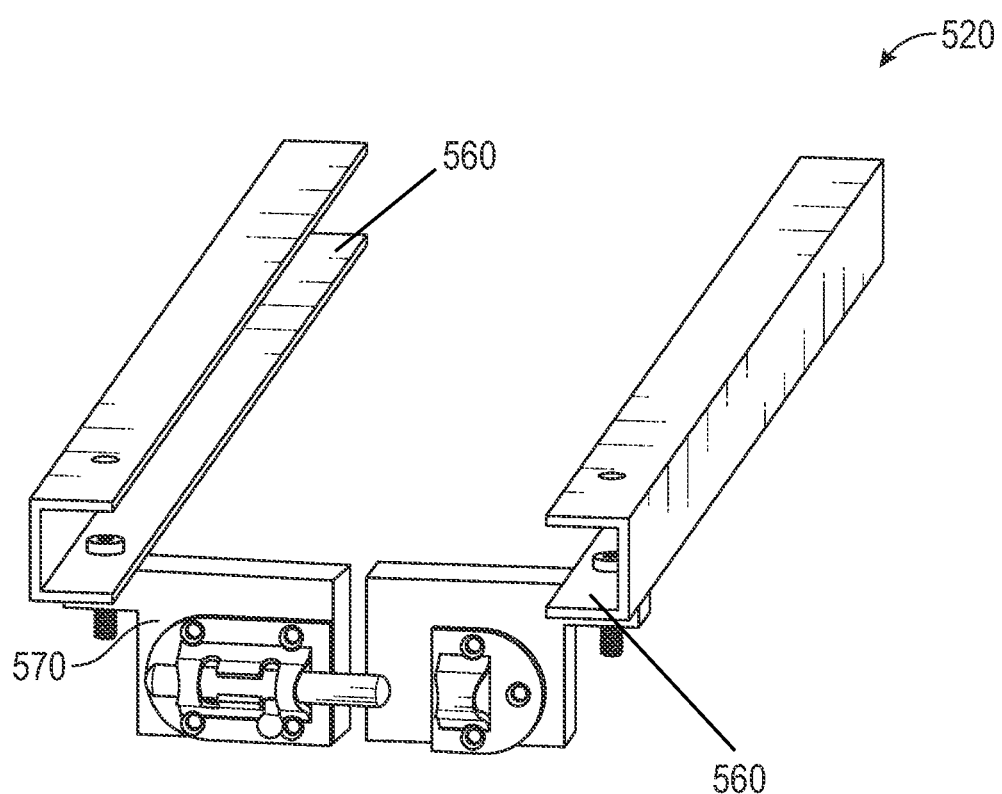
FIG. 12 is a top perspective view of a manifold support structure with a locking mechanism.

The manifold can be permanently or removable attached in the rinse tank. In some aspects, the manifold is removably attached in the rinse tank. In some aspects, the manifold comprises protruding edges and the manifold support structure comprises channels operable to engage the protruding edges of the manifold. When the manifold is removably attached to the rinse tank, the manifold support structure can further comprise a locking mechanism operable to secure the manifold to the manifold support structure. Locking mechanisms will vary depending on the mechanical attachment method used to attach the manifold, and are known in the art. In one aspect, when the manifold is removably attached to the rinse tank using channels and a lip, the locking mechanism is as shown in FIG. 12.

A washing appliance can comprise any number of manifolds depending on the particular application. For instance, a washing appliance can comprise 1, 2, 3, 4, 5, 6, 7, 8, 9, 10, or more manifolds. In some aspects, the washing appliance comprises one manifold. In other aspects, the washing appliance comprises two manifolds. In some aspects, the washing appliance comprises four manifolds.

The manifold comprises device attachment points at a second manifold surface opposite the first surface of the manifold. The attachment points are operable to removably accept a device attachment accessory, wherein the device attachment accessory is operable to hang a device in a volume of space extending along the longitudinal axis below the manifold in the interior space of the rinse tank.

The number of attachment points as well as the types of attachment accessory can and will vary depending on the intended application. The manifold can comprise 1, 5, 10, 15, 20, 25, 30, 35, 40, 45, 50, 55, 60, 65, 70, 75, 80, 85, 90, 95, or 100 attachment points or more. In some aspects, the manifold comprises forty-eight attachment points.

Further, the type of device attachment accessory can and will vary depending on the device to be washed. Any accessory that can be used to attach or hang an item can be used as device attachment accessory. As described above, when the device to be washed is a medical device used during cardiovascular procedures (cath lab) and accessory devices, non-limiting examples of medical devices and accessories include medical devices comprising lumens, catheters, endoscopes, dilators, dilator accessories, introducer sheaths, guidewires, balloons, vascular closure devices, atherectomy devices, fractional flow reserve (FFR) wires, racetrack tubing, cables and wiring, medical tubing, and hypodermic, transseptal, and other needles. Accordingly, a device attachment accessory can be any type of accessory that can be operable to hang medical devices comprising lumens, catheters, endoscopes, dilators, dilator accessories, introducer sheaths, guidewires, balloons, vascular closure devices, atherectomy devices, fractional flow reserve (FFR) wires, racetrack tubing, cables and wiring, medical tubing, and hypodermic, transseptal, and other needles in the rinse tank. For instance, when a device to be washed is a guidewire, the device attachment accessory can be a hook connected to the attachment point, upon which the guidewire can be hung. Alternatively, when the device to be hung is a device comprising a lumen comprising a Luer connector, the device attachment accessory can be a Luer connector connected to the attachment point. It will be recognized that a manifold can comprise more than one type of attachment accessory to hang more than type of device on the same manifold. Further, a manifold can have all attachment points in use during cleaning. Alternatively, a manifold can have a fraction of the attachment points in use during cleaning.

In some aspects, the washing appliance can be used to wash the lumen of a device comprising a lumen. When the device is used for washing the lumen of a lumen device, the manifold further comprises a wash fluid opening in the manifold to which one end of a wash fluid adapter can be connected. A second end of the wash fluid adapter can extend through the rinse wall and can be in fluid communication with a source of wash fluid. When the device is used for washing the lumen of a lumen device, the one or more of the attachment points also comprise a wash fluid delivery opening for delivery of wash fluid to the lumen of an attached device. The wash fluid delivery opening is in fluid communication with the source of wash fluid through a wash fluid flow path extending from the wash fluid delivery opening to the source of wash fluid through a manifold channel in the manifold extending between the wash fluid delivery opening and the wash fluid opening or the wash fluid adapter opening.

(e) Other Components

The washing appliance can further comprise other components that can aid in cleaning of devices or optimize cleaning parameters. Non limiting examples of other components include sensors, filters, connectors, probes, samplers, connectors valves, other devices, seals, gaskets other fluid containment and control elements to direct the spray fluid and wash fluid during operation of the washing appliance.

In some aspects, the washing appliance further comprises a pressure pump or compressor (not shown) and associated piping and control valves and mechanisms disposed between the spray fluid opening and the spray fluid source (not shown), wherein the pressure pump causes the spray fluid to spray from the one or more nozzles at a predetermined pressure and/or deliver wash fluid to the lumen of a lumen device. In other aspects, pressure can be provided gravity using tanks placed at a height suitable for providing pressure.

Non-limiting examples of sensors that may be used in conjunction with a washing device of the instant disclosure include sensors for fluid flow, temperature, pH, oxygen, pressure, concentration, and sensors that can detect specific compounds in a wash or spray fluid. Fluid flow sensors can sense the rate of reagent or solvent addition which can be adjusted in an adaptive response to real time, or near real time, touchless measurements. Other devices can include compression fittings, quick disconnects, aseptic G sterile connectors and other such fitting that would allow for the creation of sterile connections, septums for sampling, filters, bearings such as agitator shaft bearings and bearing assemblies, viewports, and probe ports.

The washing appliances of the instant disclosure can further comprise contact or contactless measuring systems, which may comprise instruments operable to measure, for example, quantity (i.e., volume, weight, etc.), cleaner or contaminant identity and/or concentration, flow rate, temperature, pressure, turbidly, color, and verifying a cleaning endpoint is reached. The measurement can be performed using spectroscopic analysis, or optical detection. Verification of cleanliness can be performed using a range of analytical instruments, such as liquid chromatography (LC), MS high performance liquid chromatography (HPLC) with or without UV—VIS, UV—VIS-DAD, and/or mass spectrometry detectors, electromagnetic radiation spectroscopy, such as UV/Vis NIRF, FTIR, and RAMAN, and combinations thereof.

A washing appliance of the instant invention can also comprise a temperature control device adapted to control the temperature of the wash or spray fluid. The temperature control device can control temperature by conductive, thermoelectric, resistance heating, impedance, temperature modulation using induction, microwave dielectric heating and any combination thereof.

The washing appliance of the instant invention can further comprise a controller in functional communication with components of the appliance such as valves, and sensors, and is operable to provide tight control of the operational sequence of the cleaning process on parameters such as temperature and pH. For instance, a controller can perform one or more of the following functions: allow switching on or off components of the washing appliance such as a fluid discharge valve, fluid inlet valve, or drain valve, provide controls for system function such as fluid pressure and provide monitoring information using data collected by the sensors. The controller can include additional input and output components that permit input by a user (e.g., a touch screen display, a keyboard, a keypad, a mouse, a button, a switch, a microphone, etc.). The controller can also include output components that provide output information (e.g., a display, a speaker, one or more light-emitting diodes (LEDs), etc.).

In addition to the controller, the device can further comprise at least one processor and associated memory adapted to receive the operational and sensor data from the controller. The processor and associated memory can be hard wired to the system or can be networked in a wired or wireless manner. The processor and associated memory can also communicate with a server or other remote computing device in order to execute specific steps. A non-transitory computer readable medium programmed to execute the methods can be loaded on the processor and associated memory or in communication with the system. In some aspects, the processor can be operable to assign one or more event times, wherein each event time indicates the time of a change in the state of a signal received from a component of the system or a sensor. In this aspect, the associated memory can be operable to receive and store the signals and/or outputs of the sensors of the device, and the one or more event times. The storage component may store information and/or software related to the operation and use of the controller. The storage component can include a random-access memory (RAM), a read only memory (ROM), and/or another type of dynamic or static storage device (e.g., a flash memory, a magnetic memory, an optical memory, etc.) that stores information and/or instructions for use by the controller.

In some aspects, it is contemplated that the processor can comprise an alarm system that can be activated in response to one or more inputs from a sensor. In these aspects, it is contemplated that the alarm system can comprise a conventional device for selectively generating optical, thermal, vibrational, and/or audible alarm signals.

(f) Aspects of a Washing Appliance

Aspects of a washing appliance 100 are shown in FIGS. 1-13. The washing appliance 100 comprises a rinse tank 110, spray assemblies 200, and manifolds 500 for hanging devices to be washed in the washing appliance 100.

The rinse tank 110 comprises an interior space 140 defined by a rinse tank top 120, a rinse tank bottom 130, and rinse tank walls 150. The rinse tank 110 also comprises a rinse tank opening 160 in the rinse tank walls 150, and access doors 170 for reversibly sealing the rinse tank opening 160. A drain 135 in the rinse tank bottom 130 is operable to drain wash and spray fluids from the washing appliance 100 during operation.

Figure 8:
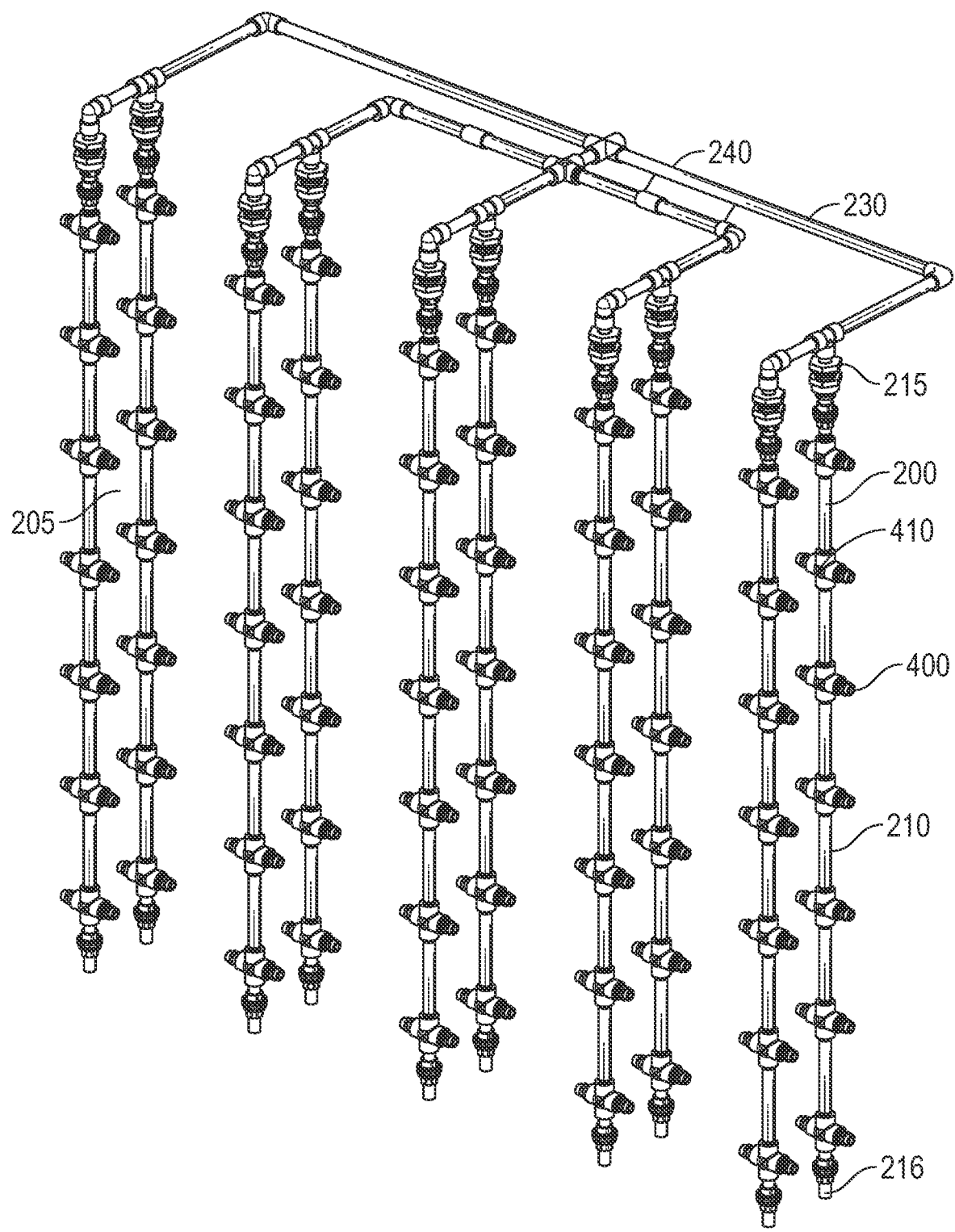
FIG. 8 is a front perspective view of a pipe assembly.

The spray assemblies 200 each comprises a spray tube 210 disposed in the interior space 140 of the rinse tank. The spray tube 210 extends through a spray tube opening 165 in the rinse tank top 120 into the rinse tank interior space 140 along a vertical longitudinal axis 180 extending from the rinse tank top 120 to the rinse tank bottom 130. The spray tube 210 comprises a spray fluid opening 220 at a spray tube proximal end 215 external to the rinse tank 110 and a spray tube distal end 216 in the rinse tank interior space 140. The spray fluid opening 220 is in fluid communication with a source of spray fluid. The spray assemblies 200 also comprise one or more nozzles 400 attached to the spray tube 210. In an aspect shown in FIGS. 1-3 and 6-8, the spray assemblies 200 each comprises seven pairs of nozzles 410 distributed along the spray assembly 200, wherein a first nozzle 400 in each pair of nozzles 410 is positioned opposite a second nozzle 400 in the pair of nozzles 410. In an aspect shown in FIGS. 1-3, the washing appliance comprises five pairs of spray assemblies 205 and four manifolds 500 disposed alternatively between the pairs of spray assemblies 205. In FIG. 8, five pairs of spray assemblies 205 are shown attached to a piping 230 to form a pipe assembly 240. In another aspect shown in FIG. 6, the washing appliance comprises three pairs of spray assemblies 205 and two manifolds 500 disposed alternatively between the pairs of spray assemblies 205.

The manifold 500 of the washing appliance 100 is attached in the rinse tank interior space 140 at a first surface 510 of the manifold 500 to a manifold support structure 520 at the rinse tank top. The manifold 500 further comprises device attachment points 530 at a second manifold surface 540 opposite the first manifold surface 510 (see e.g., FIG. 9). In the aspect shown in the figures, the manifold 500 comprises forty-eight device attachment points 530. The manifold 500 is operable to suspend an attached device 600 in a volume of space 190 extending along the longitudinal axis 180 below the manifold 500 in the rinse tank interior space 140, and the one or more nozzles 400 are operable to spray the spray fluid into the volume of space 190.

Figure 2:
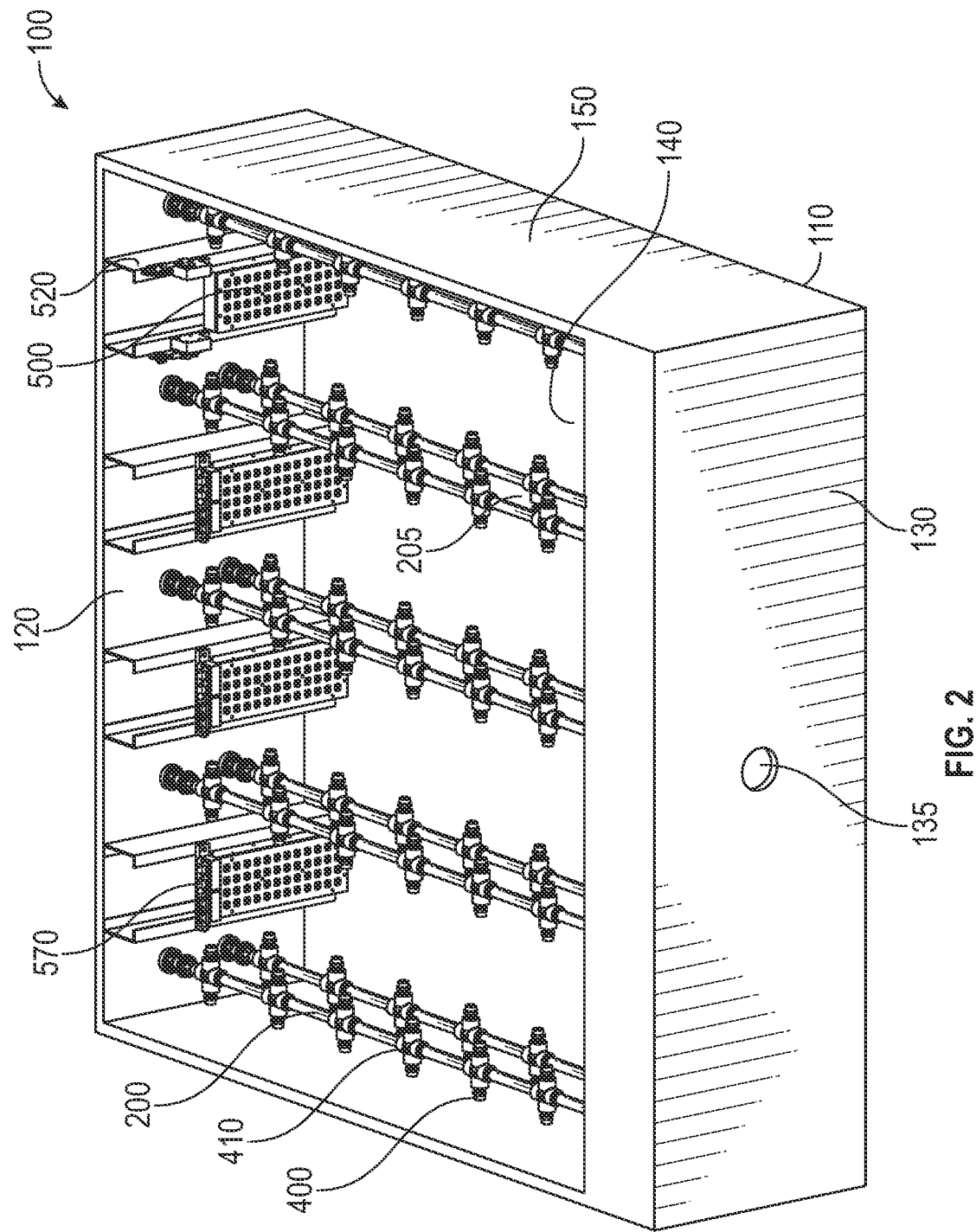
FIG. 2 is a bottom perspective view of the front of the washing appliance of FIG. 1.
Figure 3:
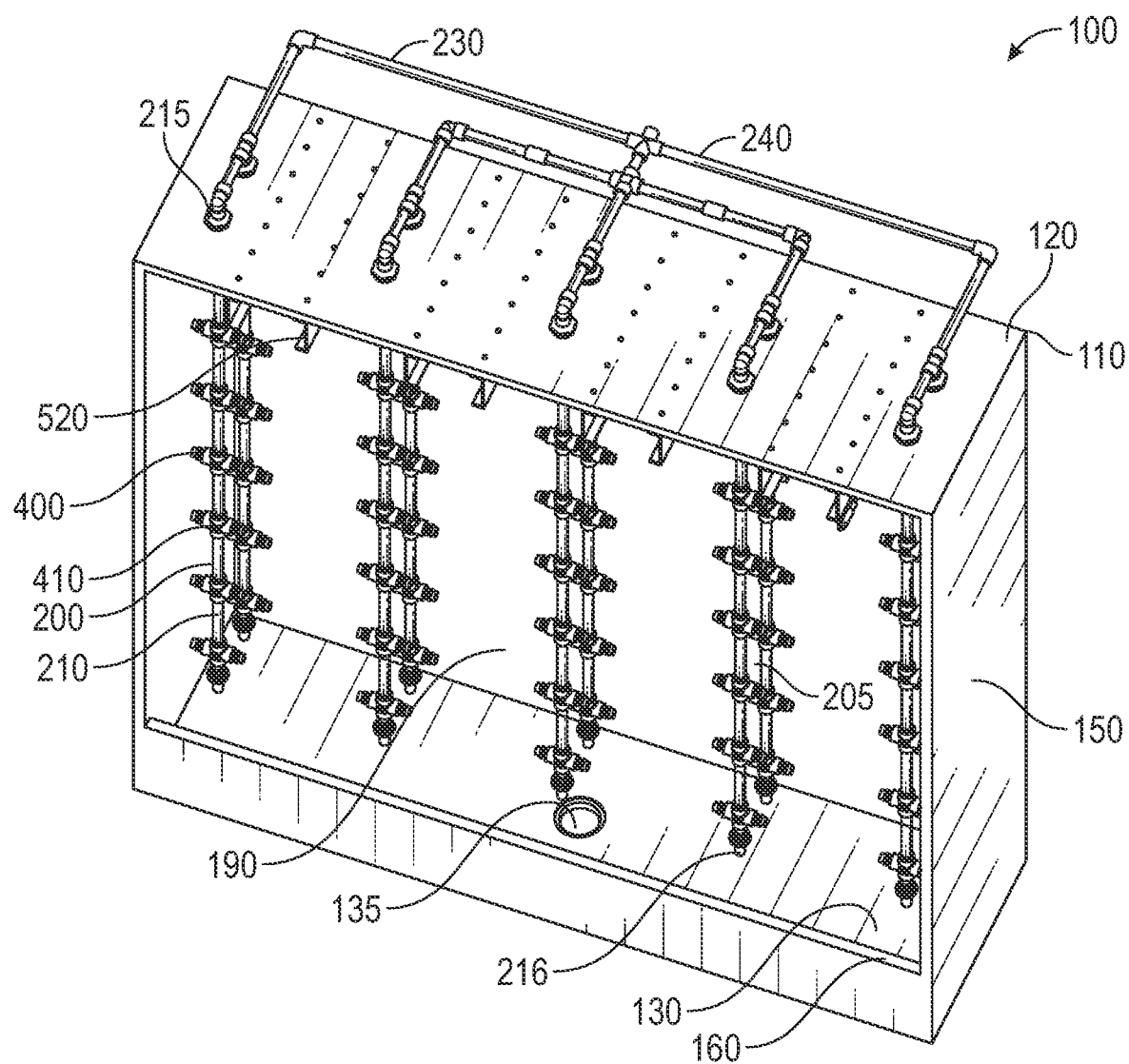
FIG. 3 is a top perspective view of the front of the washing appliance of FIG. 1.
Figure 4:
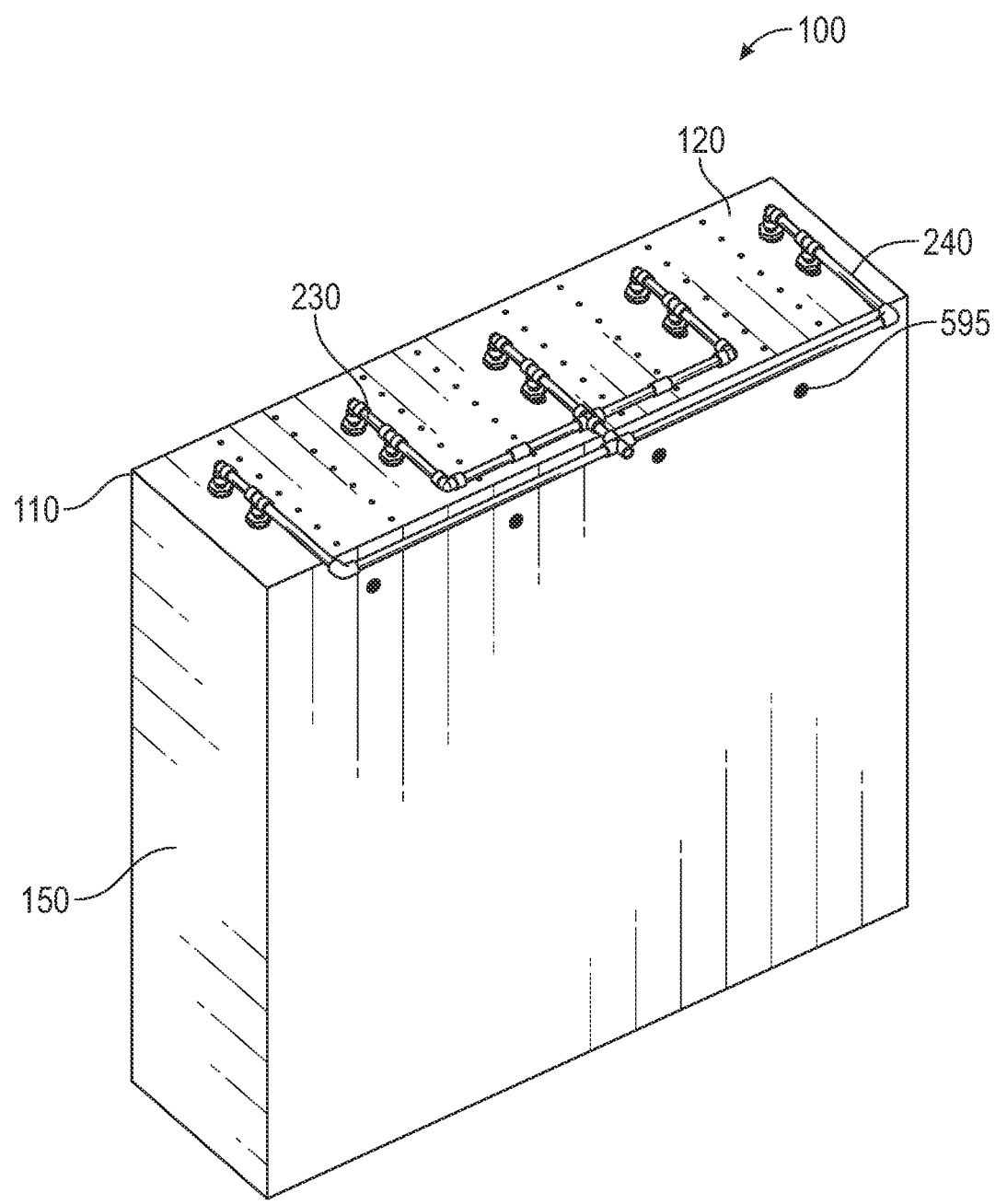
FIG. 4 is a top perspective view of the back of the washing appliance of FIG. 1.
Figure 5:
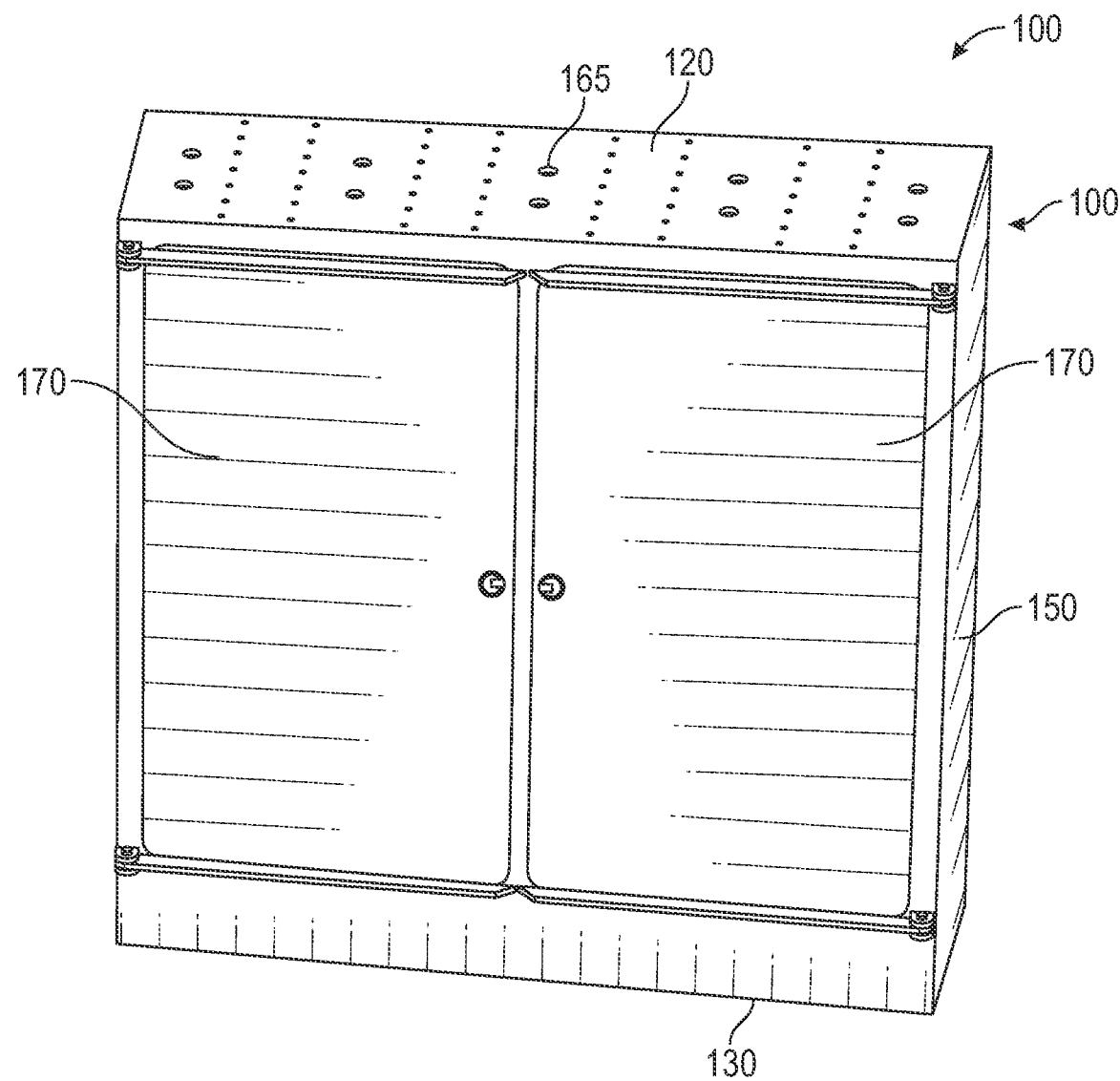
FIG. 5 is a top perspective view of the front of a sink tank of a washing appliance of the instant disclosure showing the access doors in a closed position, sealing the rinse tank opening.
Figure 6:
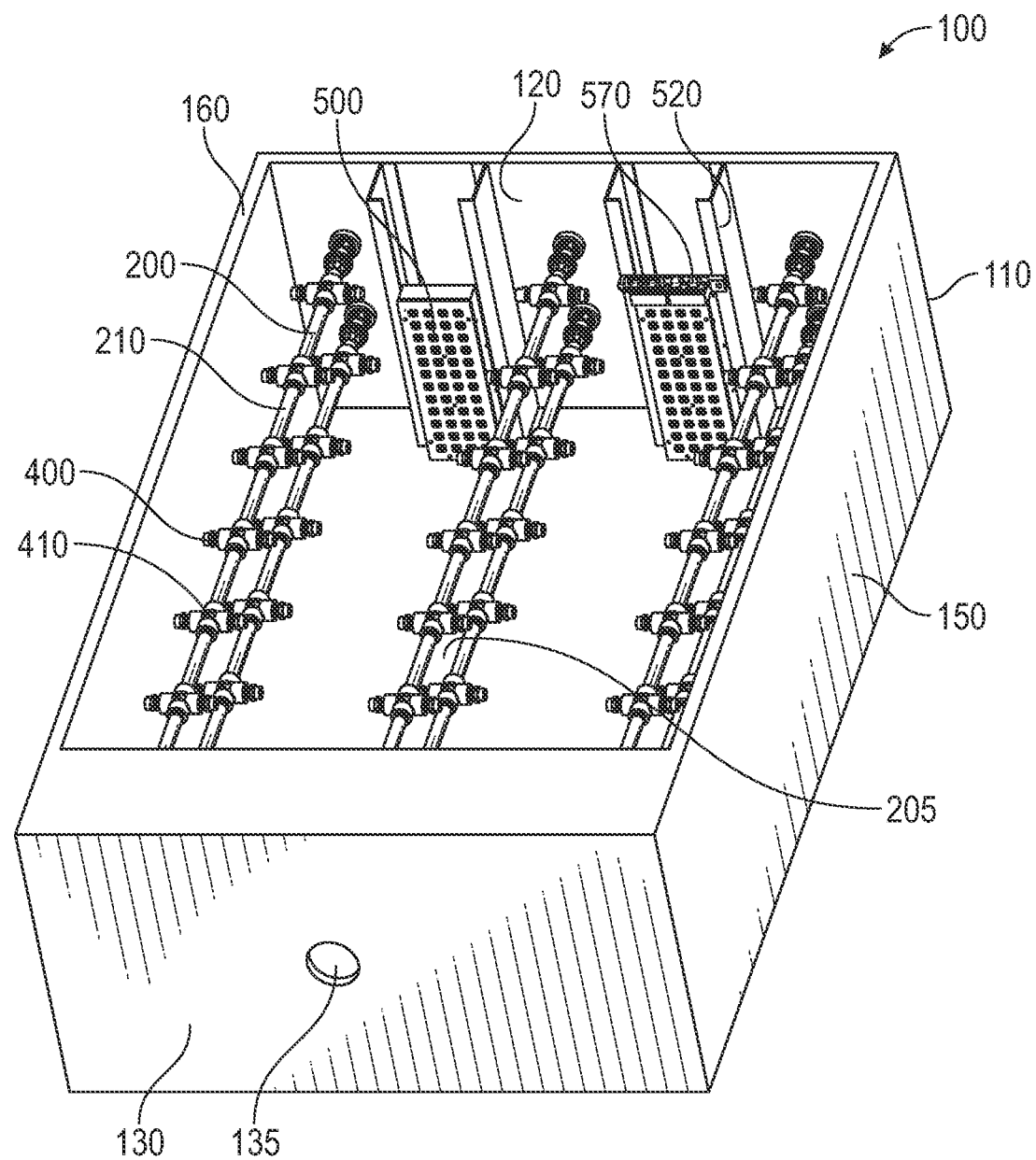
FIG. 6 is a bottom perspective view of a washing appliance of the instant disclosure comprising two manifolds. The access door is not shown.
Figure 7:
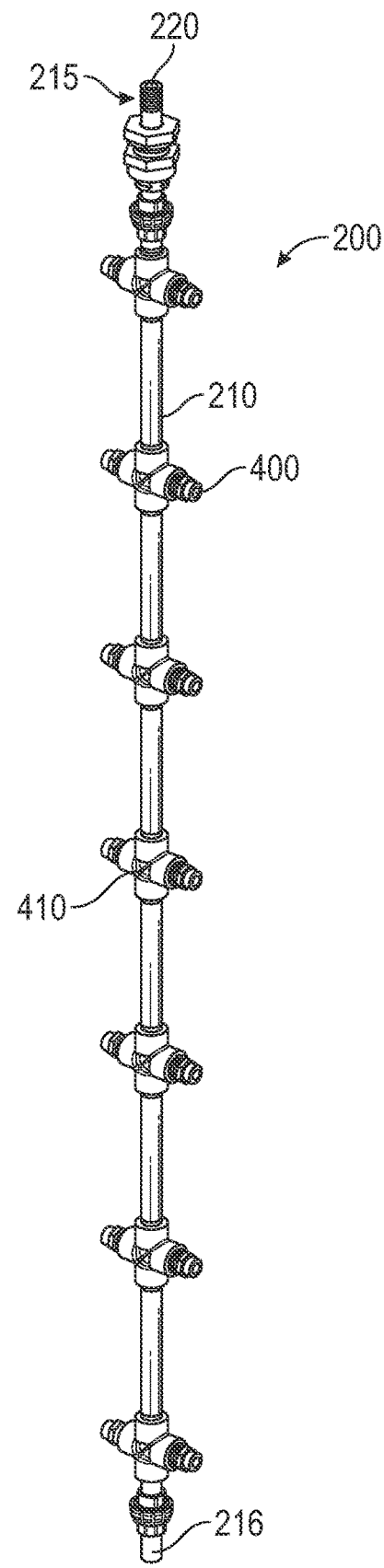
FIG. 7 is a front view of a spray assembly.

The manifold 500 in the aspects shown in the figures comprises protruding edges 550 and the manifold support structure 520 comprises channels operable to engage the protruding edges 550 of the manifold 500 to attach the manifold to the rinse tank top 120. The manifold support structure 520 further comprises a locking mechanism 570 operable to secure the manifold 500 to the manifold support structure 520. The manifold support structure 520 with a locking mechanism is shown in FIG. 12. FIGS. 1 and 2 show three manifolds 500 attached and secured to manifold support structures 520 using the locking mechanism 570 and one manifold 500 attached to a manifold support structure 520 without a locking mechanism 570.

Figure 9:
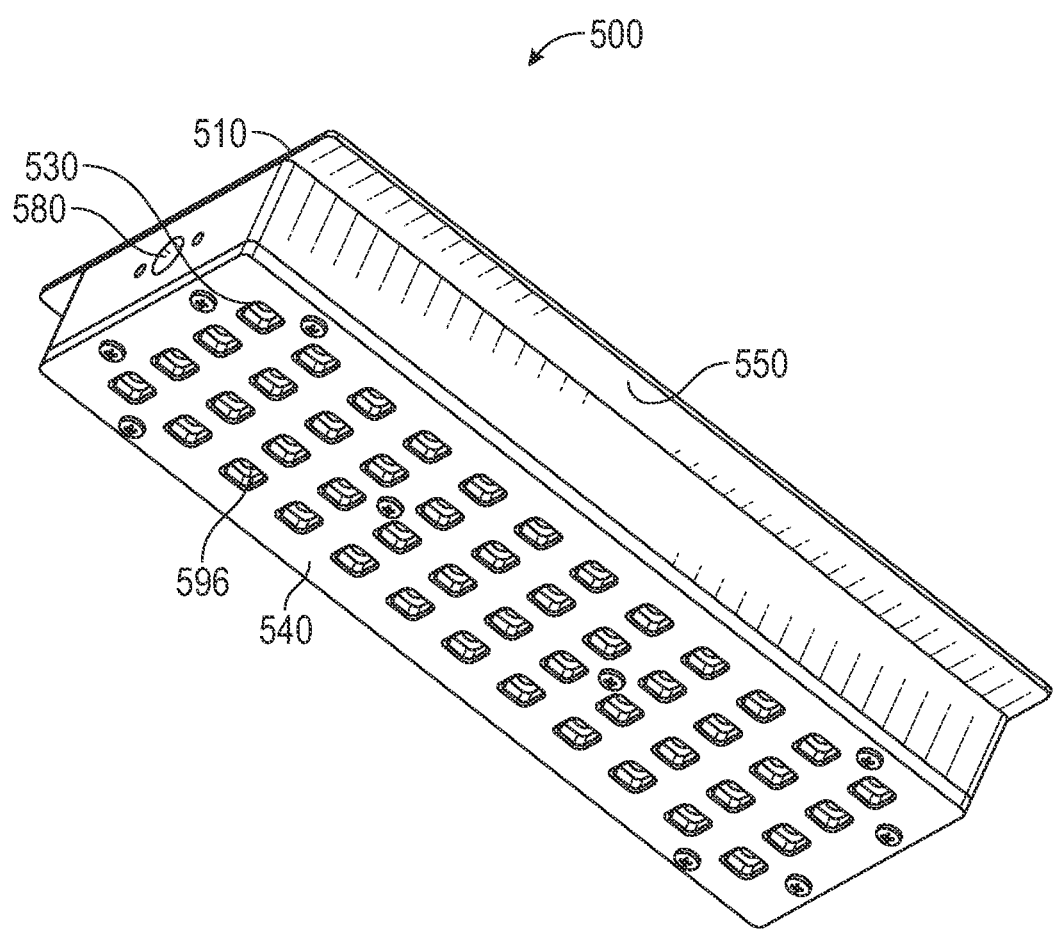
FIG. 9 is a side perspective view of a manifold of the instant disclosure.
Figure 10:
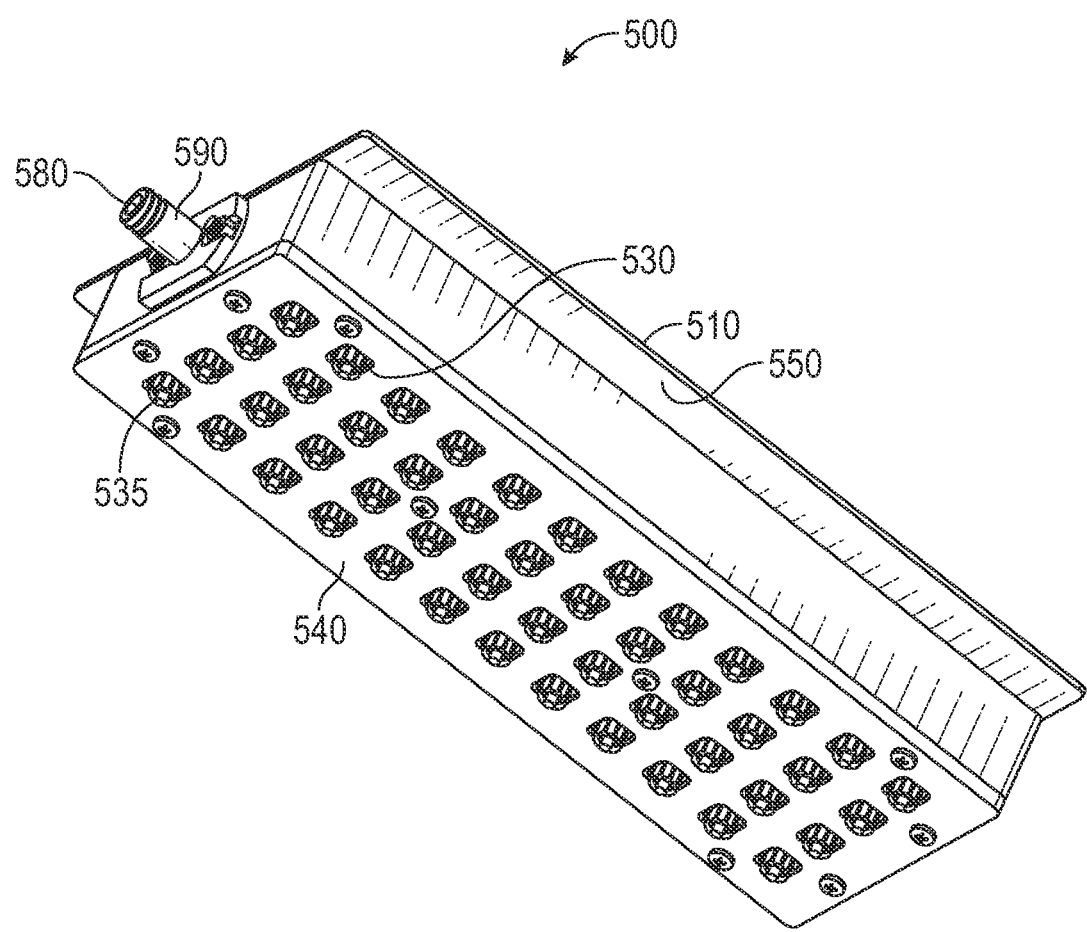
FIG. 10 is a side perspective view of a manifold of the instant disclosure.
Figure 11:
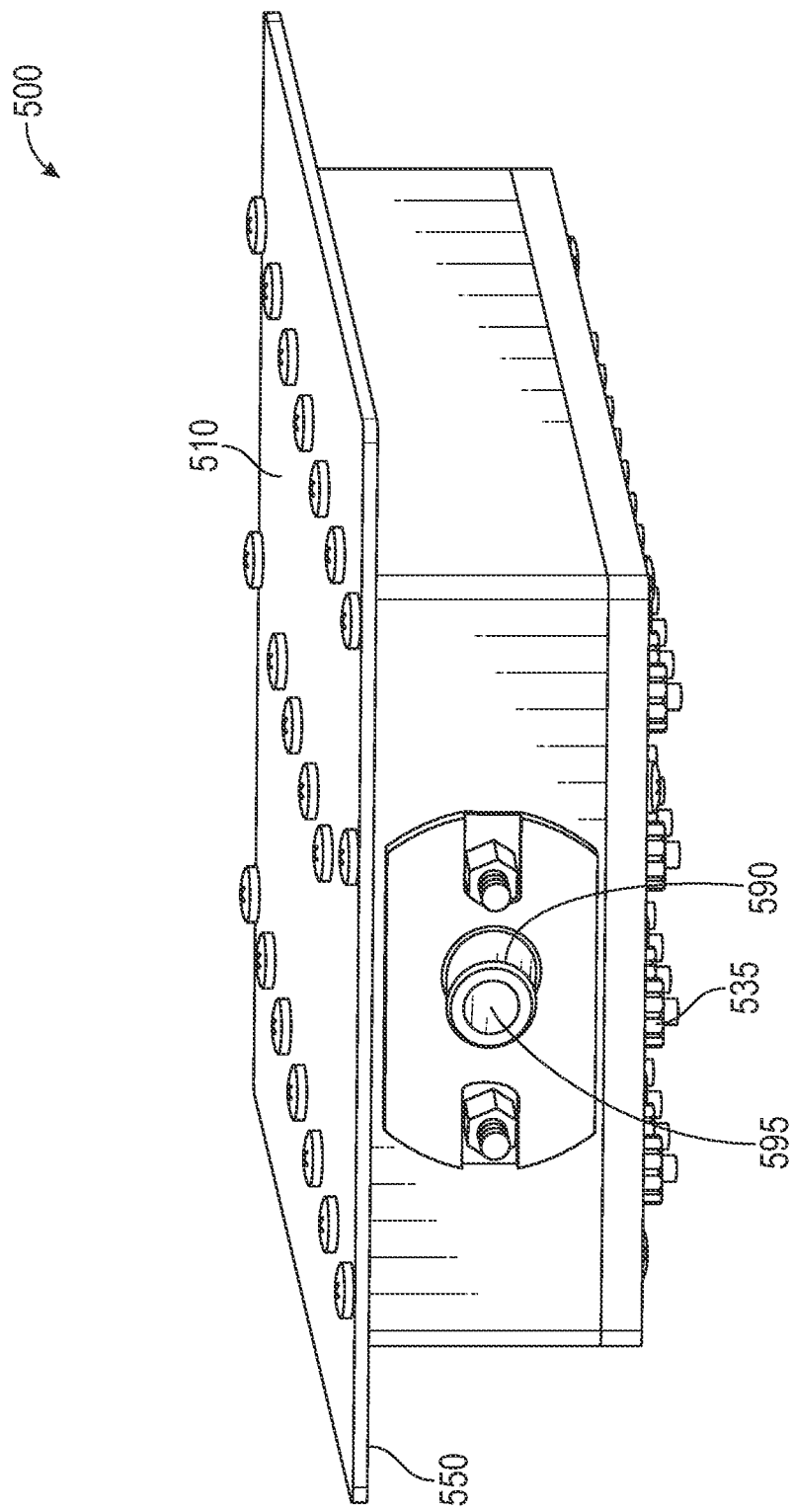
FIG. 11 is a side perspective view of a manifold of the instant disclosure.

In the aspect shown in FIGS. 9 and 10, the manifold 500 comprises a wash fluid adapter 590 connected to a wash fluid opening 580 in the manifold 500 and extending through a wash fluid adapter opening 595 (shown in FIG. 4) in the rinse tank walls 150.

the device attachment points 530 comprise wash fluid delivery openings 596. The wash fluid delivery openings 596 are in fluid communication with a source of wash fluid through a wash fluid flow path extending from the source of wash fluid, through the wash fluid adapter 590 and a manifold channel (not shown) in the manifold 500 extending between the wash fluid opening 580 to the wash fluid delivery openings 596. In the aspect shown in FIGS. 9 and 10, wash fluid adapters 590, here Luer connectors, connected to the wash fluid delivery openings 596 in the manifold 500.

Figure 13:
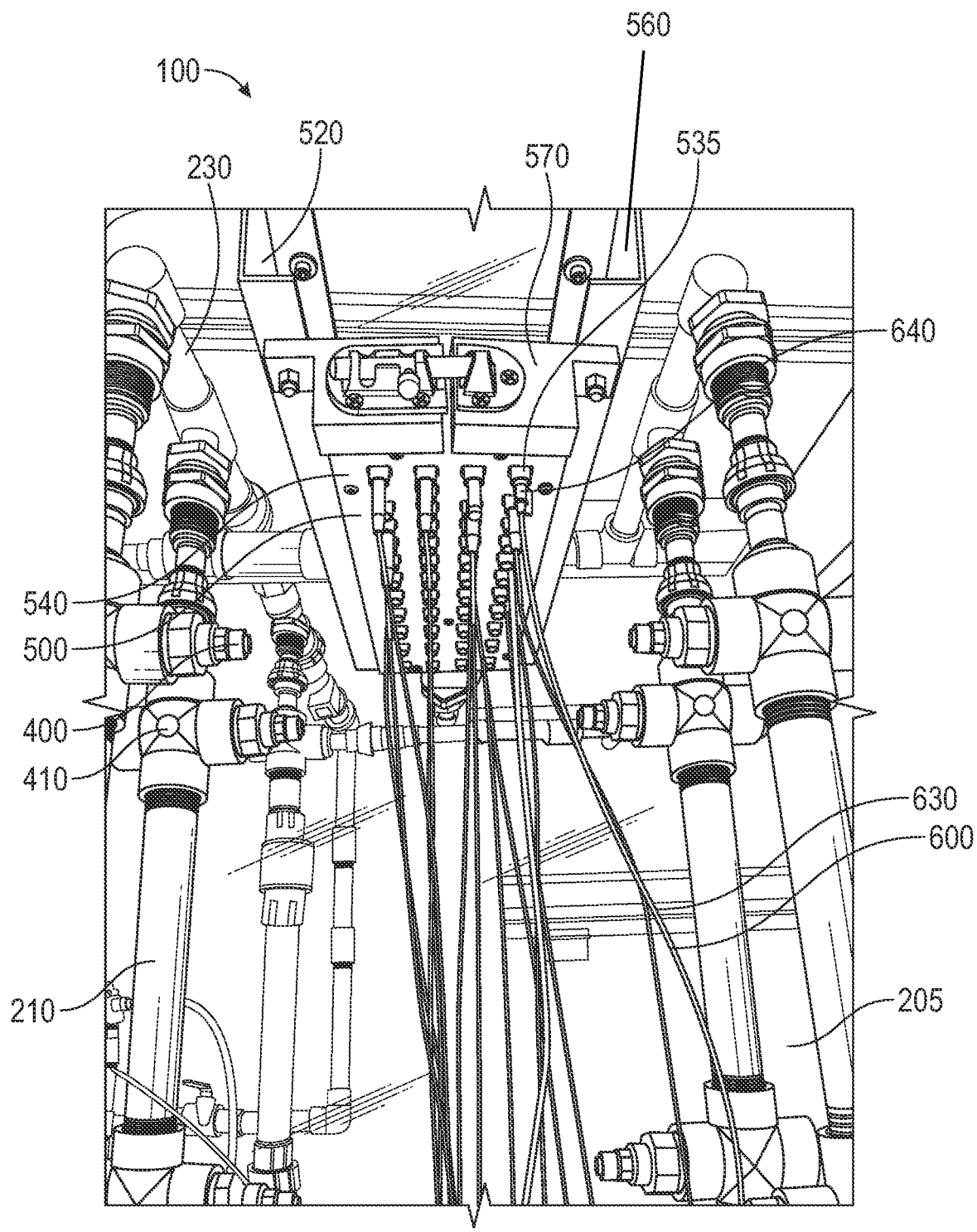
FIG. 13 shows part of a washing appliance during use with lumen devices.

FIG. 13 shows the washing appliance 100 with devices 600 comprising lumens 630 attached to the manifold 500 using Luer connector device attachment accessory 535. The devices 600 comprise fluid delivery connectors 640. Each device 600 is attached to the manifold 500 and is suspended below the manifold 500.

II. Method of Washing a Device

The instant invention also encompasses a method of cleaning a device comprising a lumen using a washing appliance described in Section (I) herein above. The device can be as described in Section I(a) herein above.

The method comprises attaching one or more devices to be washed to device attachment accessories of a manifold. The method can further comprise attaching device attachment accessories to the attachment points of the manifold appropriate for hanging the device or devices to be washed. After the one or more devices are attached to the manifold, the manifold is attached and optionally secured to the manifold support structure in the interior space of the rinse tank. The method further comprises washing exterior surfaces of the device by attaching the spray fluid opening of the spray assembly to a source of cleaning fluid by attaching piping extending from the spray fluid opening to the source of cleaning fluid and spraying the exterior surfaces of the device with cleaning fluid to thereby washing the exterior surfaces of the device. In some aspects, the method further comprises drying the exterior surface of the device by spraying the exterior surface with drying fluid.

In some aspects, the device is a lumen device. When the device is a lumen device, the method can further comprise cleaning the lumen of the device concurrently or sequentially with cleaning the exterior of the device. Clean the lumen of a lumen device can comprise attaching the wash fluid opening of the manifold to a source of cleaning fluid by attaching piping extending from the wash fluid opening of the manifold to the source of cleaning fluid. The method further comprises flushing the lumen of the device with the cleaning fluid at a predetermined flow rate or pressure. As with cleaning the exterior of a device, the lumen of the device can optionally be dried by flushing the lumen of the device with drying fluid. It will be recognized that in some aspects, only the lumen of the lumen device can be cleaned without also cleaning the exterior of the device. Accordingly, a method of cleaning a lumen device can comprise cleaning the exterior of the lumen device, cleaning the lumen, or both.

The duration of during which the device is sprayed or flushed can and will vary depending on the device, the type of contaminants to be washed, the degree of contamination (dirtiness) of the device to be cleaned, the parameters used during cleaning such as pressure and volume of cleaning fluid, and the cleaning fluid among other variables or any combination thereof. In essence, a device is sprayed with the cleaning fluid until a predetermined cleanliness endpoint is determined. A cleaning endpoint can be determined while using the washing appliance. Alternatively, cleanliness endpoint can be a predetermined cleanliness endpoint such as an endpoint determined by regulatory authorities. Non-limiting examples of cleanliness standards for re-usable medical devices established by regulatory authorities include:

ASTM E2314: Standard Test Method for Determination of Effectiveness of Cleaning Processes for Reusable Medical Instruments Using a Microbiologic Method (Simulated Use Test)

ASTM D7225: Standard Guide for Blood Cleaning Efficiency of Detergents and Washer-Disinfectors ASTM F3208: Standard Guide for Selecting Test Soils for Validation of Cleaning Methods for Reusable Medical Devices ASTM F3172: Standard Guide for Validating Cleaning Processes Used During the Manufacture of Medical Devices Guidelines for reprocessing reusable medical devices, such as orthoscopic shavers, endoscopes, and suction tubes established by the FDA The methods of the instant disclosure can further comprise developing protocols for cleaning a device to reach a desired cleaning endpoint for that specific device. For instance, the duration of wash, the pressure and flow of liquids, the cleaning and drying fluids can all be adjusted to develop a protocol for cleaning the device.

The methods of the instant disclosure can further comprise developing protocols for determining when a cleaning endpoint is reached for a specific device. For instance, a protocol for determining when a cleaning endpoint is reached for a bloody device can comprise assaying used or recirculated cleaning fluid for the presence of blood residue, wherein the device is considered clean when a certain concentration of blood residue, the cleaning endpoint, is reached. Established or newly developed test methods can be used.

One or more than one cleaning fluid can be used in a method of cleaning a certain device. For instance, the device can first be cleaned with water to hydrate dirt and contaminants on and in the device, followed by cleaning with a cleaning fluid appropriate for the device, the contaminants, or both.

Cleaning fluid can and will vary depending on the device, the type of contaminants to be washed, the degree of contamination (dirtiness) of the device to be cleaned, the parameters used during cleaning such as pressure and volume of cleaning fluid, and the cleaning fluid among other variables or any combination thereof. Appropriate cleaning fluids are known in the art. Non-limiting examples of cleaning fluids appropriate for cleaning devices using a method of the instant disclosure include disinfectants, germicides, sanitizers, soaps, enzymes, alcohols, solvents, or any combination thereof among others.

Similarly, drying fluid can and will vary depending on the device, the cleaning fluid(s) used, the parameters used during cleaning such as pressure and volume of cleaning fluid, and the drying fluid among other variables or any combination thereof. Appropriate drying fluids are known in the art. Non-limiting examples of drying fluids appropriate for drying devices using a method of the instant disclosure include air such as ambient air, nitrogen, or oxygen, alcohols, solvents, and any combination thereof among others.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

A "genetically modified" cell refers to a cell in which the nuclear, organellar or extrachromosomal nucleic acid sequences of a cell has been modified, i.e., the cell contains at least one nucleic acid sequence that has been engineered to contain an insertion of at least one nucleotide, a deletion of at least one nucleotide, and/or a substitution of at least one nucleotide.

The terms "genome modification" and "genome editing" refer to processes by which a specific nucleic acid sequence in a genome is changed such that the nucleic acid sequence is modified. The nucleic acid sequence may be modified to comprise an insertion of at least one nucleotide, a deletion of at least one nucleotide, and/or a substitution of at least one nucleotide. The modified nucleic acid sequence is inactivated such that no product is made. Alternatively, the nucleic acid sequence may be modified such that an altered product is made.

The term "heterologous" refers to an entity that is not native to the cell or species of interest.

The terms "nucleic acid" and "polynucleotide" refer to a deoxyribonucleotide or ribonucleotide polymer, in linear or circular conformation. For the purposes of the present disclosure, these terms are not to be construed as limiting with respect to the length of a polymer. The terms may encompass known analogs of natural nucleotides, as well as nucleotides that are modified in the base, sugar and/or phosphate moieties. In general, an analog of a particular nucleotide has the same base-pairing specificity, i.e., an analog of A will base-pair with T. The nucleotides of a nucleic acid or polynucleotide may be linked by phosphodiester, phosphothioate, phosphoramidite, phosphorodiamidate bonds, or combinations thereof.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

As used herein, the terms "target site", "target sequence", or "nucleic acid locus" refer to a nucleic acid sequence that defines a portion of a nucleic acid sequence to be modified or edited and to which a homologous recombination composition is engineered to target.

The terms "upstream" and "downstream" refer to locations in a nucleic acid sequence relative to a fixed position. Upstream refers to the region that is 5' (i.e., near the 5' end of the strand) to the position, and downstream refers to the region that is 3' (i.e., near the 3' end of the strand) to the position.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences may also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

As various changes could be made in the above-described cells and methods without departing from the scope of the invention, it is intended that all matter contained in the above description and in the examples given below, shall be interpreted as illustrative and not in a limiting sense.

What is claimed is:

1. A washing appliance 100 for washing a medical device comprising a lumen and accessories (lumen device), the washing appliance 100 comprising:
    a. a rinse tank 110 comprising:
        i. a rinse tank interior space 140 defined by a rinse tank top 120, a rinse tank bottom 130, and rinse tank walls 150;
        ii. an access door 170 for reversibly sealing a rinse tank opening 160 in the rinse tank walls 150; and
        iii. a drain 135 in the rinse tank bottom 130;
    b. a spray assembly 200 comprising:
        i. a spray tube 210 extending through a spray tube opening 165 in the rinse tank top 120 into the rinse tank interior space 140 along a vertical longitudinal axis 180 extending from the rinse tank top 120 to the rinse tank bottom 130, the spray tube 210 comprising a spray fluid opening 220 at a spray tube proximal end 215 external to the rinse tank 110, a spray tube distal end 216 in the rinse tank interior space 140, wherein the spray fluid opening 220 is in fluid communication with a source of spray fluid;
        ii. one or more nozzles 400 attached to the spray tube 216; and
        iii. a manifold support structure 520 at the rinse tank top 120, wherein the manifold support structure 520 comprises a locking mechanism 570; and
    c. a manifold 500 removably attached in the rinse tank interior space 140 at a first surface 510 of the manifold 500 to the manifold support structure 520, wherein the manifold 500 comprises:
        i. a wash fluid adapter 590 connected to a wash fluid opening 580 in the manifold 500 and extending through a wash fluid adapter opening 595 in the rinse tank walls 150;
        ii. device attachment points 530 at a second surface 540 of the manifold 500 opposite the first surface 510, wherein one or more of the attachment points 530 comprise a wash fluid delivery opening 596 in fluid communication with a source of wash fluid through a wash fluid flow path extending from the wash fluid delivery opening 595 to the source of wash fluid through a manifold channel in the manifold 500 extending between the wash fluid delivery opening 596 and the wash fluid opening 580 or the wash fluid adapter opening 595;
        iii. one or more device attachment accessory 535 operable to hang a lumen device in a volume of space 190 extending along the longitudinal axis 180 below the manifold 500 in the rinse tank interior space 140;
    wherein the manifold 500 comprises protruding edges 550 and the manifold support structure 520 comprises channels 560 operable to engage the protruding edges 550 of the manifold 500, wherein the locking mechanism 570 is operable to secure the manifold 500 to the manifold support structure 520, and wherein the one or more nozzles 400 are operable to spray the spray fluid into the volume of space 190.

2. The washing appliance of claim 1, wherein the lumen device is used during a cardiovascular procedure (cath lab) and accessory devices.

3. The washing appliance of claim 1, wherein the lumen device is a catheter, an endoscope, a closure device, an accessory device to a catheter or endoscope, or any combination thereof.

4. The washing appliance of claim 1, wherein the lumen device is a catheter, an endoscope, a dilator, an introducer, medical tubing, racetrack tubing, a guide wire, a cable, or any combination thereof.

5. The washing appliance of claim 1, wherein the lumen device is an unused originally manufactured device (OM), a used OM device, an unused reprocessed device, or a used reprocessed device.

6. The washing appliance of claim 1, wherein the spray assembly comprises seven pairs of nozzles, wherein a first nozzle in a pair of nozzles is positioned opposite a second nozzle in the pair of nozzles.

7. The washing appliance of claim 1, wherein the washing appliance comprises three or more pairs of spray assemblies and two or more manifolds disposed alternatively between the pairs of spray assemblies.

8. The washing appliance of claim 1, wherein the washing appliance comprises three pairs of spray assemblies and two manifolds disposed alternatively between the pairs of spray assemblies.

9. The washing appliance of claim 1, wherein the washing appliance comprises five pairs of spray assemblies and four manifolds disposed alternatively between the pairs of spray assemblies.

10. The washing appliance of claim 1, wherein the washing appliance further comprises a pressure pump or compressor disposed between the spray fluid opening of the spray tube and the spray fluid source, wherein the pressure pump or compressor causes the spray fluid to spray from the one or more nozzles at a predetermined pressure or flow rate.

11. The washing appliance of claim 1, wherein the fluid comprises a cleaning and/or drying agent.

12. The washing appliance of claim 1, wherein the fluid is liquid or air.

13. The washing appliance of claim 1, wherein the manifold comprises forty-eight attachment points.

14. The washing appliance of claim 1, wherein the device attachment accessory 535 is a Luer connector attachment accessory connected to the attachment point 530.

15. The washing appliance of claim 14, wherein the device is a lumen device comprising a Luer connector 640 in fluid communication with the lumen 630 of the device.

16. The washing appliance of claim 15, wherein the washing appliance further comprises one or more lumen devices 600 comprising a Luer connector 640 attached to the Luer connector attachment accessory 535.

17. The washing appliance of claim 16, wherein the washing appliance further comprises a pressure pump or compressor disposed between the wash fluid opening and the wash fluid source, wherein the pressure pump or compressor causes the wash fluid to flow through the lumen of the device at a predetermined flow rate.

18. The washing appliance of claim 1, wherein the washing appliance further comprises connectors, valves, sensors such as pressure sensors and flow meters, seals, gaskets, and other fluid containment and control elements to direct the spray fluid and wash fluid during operation of the washing appliance.

* * * * *